United States Patent
Zhou

(10) Patent No.: US 12,311,098 B2
(45) Date of Patent: May 27, 2025

(54) VACUUM OSCILLATION PREVENTION IN A VENTURI SURGICAL SYSTEM

(71) Applicant: Alcon Inc., Fribourg (CH)

(72) Inventor: Jiansheng Zhou, Cerritos, CA (US)

(73) Assignee: Alcon Inc., Fribourg (CH)

( * ) Notice: Subject to any disclaimer, the term of this patent is extended or adjusted under 35 U.S.C. 154(b) by 1031 days.

(21) Appl. No.: 17/146,665

(22) Filed: Jan. 12, 2021

(65) Prior Publication Data

US 2021/0213183 A1 Jul. 15, 2021

Related U.S. Application Data

(60) Provisional application No. 62/960,777, filed on Jan. 14, 2020.

(51) Int. Cl.
*A61M 1/00* (2006.01)
*A61F 9/007* (2006.01)

(52) U.S. Cl.
CPC .......... *A61M 1/804* (2021.05); *A61F 9/00736* (2013.01); *A61M 2205/3331* (2013.01); *A61M 2205/50* (2013.01)

(58) Field of Classification Search
CPC .......... A61M 1/804; A61M 2205/3331; A61M 2205/50; A61F 9/00736; G05B 11/42; G05D 16/024; G05D 16/2013
See application file for complete search history.

(56) References Cited

U.S. PATENT DOCUMENTS

| | | | |
|---|---|---|---|
| 4,838,281 A | 6/1989 | Rogers et al. | |
| 4,850,377 A | 7/1989 | Parker et al. | |
| 5,354,268 A * | 10/1994 | Peterson | A61M 1/74 604/35 |
| 5,674,194 A * | 10/1997 | Jung | A61M 1/743 604/118 |
| 7,524,299 B2 | 4/2009 | Hopkins | |
| 10,314,741 B2 * | 6/2019 | Sorensen | A61M 1/72 |

(Continued)

FOREIGN PATENT DOCUMENTS

| EP | 0770940 A1 | 5/1997 |
|---|---|---|
| EP | 3627244 A1 | 3/2020 |

OTHER PUBLICATIONS

Encyclopedia Britannica, Inc., 2024, https://www.britannica.com/search?query (Year: 2024).*

*Primary Examiner* — Mohammad Ali
*Assistant Examiner* — Sheela Rao

(57) ABSTRACT

Control methods for generating a venturi vacuum in a substantially oscillation-free manner for a surgical system. The control methods generally include utilizing real-time readings from a venturi vacuum generator inlet pressure transducer and a vacuum pressure transducer on the vacuum side of the venturi vacuum generator. These values may be employed in real-time to ascertain the emergence of an oscillation region on the vacuum side which may then be addressed by way of a bleed control proportional valve. When employed in combination with a throttle control proportional valve at the inlet side of the venturi vacuum generator, pressures may be manipulated in light of one another and/or individually as directed through a central controller. Thus, the presentation of oscillations on the vacuum side may be avoided to provide for a more stable vacuum supported surgical procedure.

6 Claims, 8 Drawing Sheets

(56) References Cited

U.S. PATENT DOCUMENTS

| | | |
|---|---|---|
| 10,795,323 B2 | 10/2020 | Skertic |
| 2009/0124962 A1 | 5/2009 | Hopkins et al. |
| 2017/0042731 A1* | 2/2017 | Kishimoto ............... A61M 1/79 |
| 2018/0207032 A1 | 7/2018 | Charles et al. |

* cited by examiner

VACUUM OSCILLATION PREVENTION IN A VENTURI SURGICAL SYSTEM

PRIORITY CLAIM

This application claims the benefit of priority of U.S. Provisional Patent Application Ser. No. 62/960,777 titled "VACUUM OSCILLATION PREVENTION IN A VENTURI SURGICAL SYSTEM," filed on Jan. 14, 2020, whose inventor is Jiansheng Zhou, which is hereby incorporated by reference in its entirety as though fully and completely set forth herein.

BACKGROUND

Over the years, many dramatic advancements have emerged in the field of minimally invasive surgeries. Whether the surgical procedure is placement of a vascular stent or performing an eye surgery, smaller, more precise instrumentation and improved techniques are now readily available. A common aspect of many minimally invasive surgeries is the use of suction during the procedure. Suction is necessary in these minimally invasive surgeries for extracting fluid, tissue, or other material. For example, in the case of eye surgery to address retina issues, it is common for suction to be used as part of a vitrectomy procedure.

Vitrectomy is the removal of some or all of the vitreous humor from a patient's eye. In some cases, the vitrectomy may constitute the majority of the procedure. A vitrectomy may accompany cataract surgery, surgery to repair a retina, to address a macular pucker, or a host of other issues.

The vitreous humor itself is a clear gel that may be removed by a vitrectomy probe when inserted through a pre-placed cannula at the eye. More specifically, during a vitrectomy procedure, the vitrectomy probe using its central channel works like a tiny guillotine and cuts vitreous into microscopic pieces at high speed. Vacuum is applied to the fluid tubing connected to the central channel, which provides suction for removal of the vitreous after it has been cut.

During a vitrectomy procedure (and other types of eye surgeries such as phacoemulsification (cataract extraction), fragmentation, and viscous fluid extraction), when vacuum is applied to extract fluid along with other material, controlling and maintaining proper Intraocular Pressure (IOP) assists the efficiency, efficacy, and safety of the surgical procedures. However, maintaining the correct IOP is a delicate balancing act between infusion and suction.

Venturi vacuum generators are commonly used in eye surgeries for providing suction. However, they may have unstable vacuum pressure or oscillation region near maximum vacuum pressure. For a venturi vacuum generator that is configured to deliver a maximum of about 670 mmHg (millimeters of mercury), there may be no oscillation at maximum operation. However, a significant amount of oscillation may occur as the vacuum generator is operated from about 550—to a level just below the 670 mmHg level. That is, as the vacuum is increased and prior to reaching the maximum vacuum, a large degree of oscillation may occur.

As noted above, vacuum pressure oscillation resulting in IOP fluctuation may affect the efficiency, efficacy, and safety of the surgical procedures. However, as a practical matter, completely avoiding such oscillation may also have drawbacks. That is, keeping the vacuum below a predetermined level may help to avoid oscillation. Unfortunately, this means keeping vacuum below a higher level which may be useful during some parts of the procedure.

Further, the option of turning on vacuum and ramping it up prior to beginning surgery so as to pass through the oscillation region before employing the probe needle may not be practical. Once more, beginning surgery by operating below the oscillation region, halting surgical maneuvering as throttling through the oscillation region, and re-starting surgical maneuvering once things settle may not be practical either. In both cases, the surgeon may not be able to operate in certain vacuum pressure settings during the procedure.

SUMMARY

A surgical system is described. The system includes a pressure source, a shutoff valve for turning on or off the supply pressure or flow to the system, and a pressure regulator for regulating the supply pressure from the source. A venturi vacuum generator is provided in communication with the supply pressure to provide vacuum pressure to a suction port of the surgical system. A throttle control proportional valve between the supply pressure regulator and the venturi vacuum generator controls flow to the vacuum generator with a vacuum pressure transducer utilized to detect a vacuum pressure exiting the venturi vacuum generator. Similarly, a venturi inlet pressure transducer is used to detect inlet pressure to the venturi vacuum generator. A bleed control proportional valve is then utilized to optionally bleed vacuum from the exit line of the venturi vacuum generator depending on these detections. Thus, a system controller configured to respond to the detections may control the throttle control proportional valve and the bleed control proportional valve to substantially prevent vacuum oscillation directed at the surgical system.

Variations of the system are available. So long as some form of dampening of oscillation from a venturi vacuum system is provided, appreciable benefit may be realized. Stated another way, driving fluid flow through a venturi vacuum generator at a level below an oscillating throttle level threshold followed by increasing the flow to reach and/or exceed the threshold while simultaneously bleeding a proportion of the vacuum flow from the generator may provide beneficial dampening or eliminating of the vacuum pressure oscillation in a manner heretofore unseen.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a vitrectomy procedure is illustrated, in which vitreous humor is removed to address retinal detachment. However, tools and control methods detailed herein may be employed in a variety of other manners. That is, the application of a venturi vacuum system of uniquely tailored, anti-oscillation features may be utilized to address vitreous hemorrhage, macular pucker, macular holes, vitreous floaters, diabetic retinopathy or a variety of other eye or even non-eye related conditions. Regardless, so long as the venturi vacuum system incorporates oscillation reduction or elimination features as detailed herein, appreciable benefit may be realized.

Figure 1:
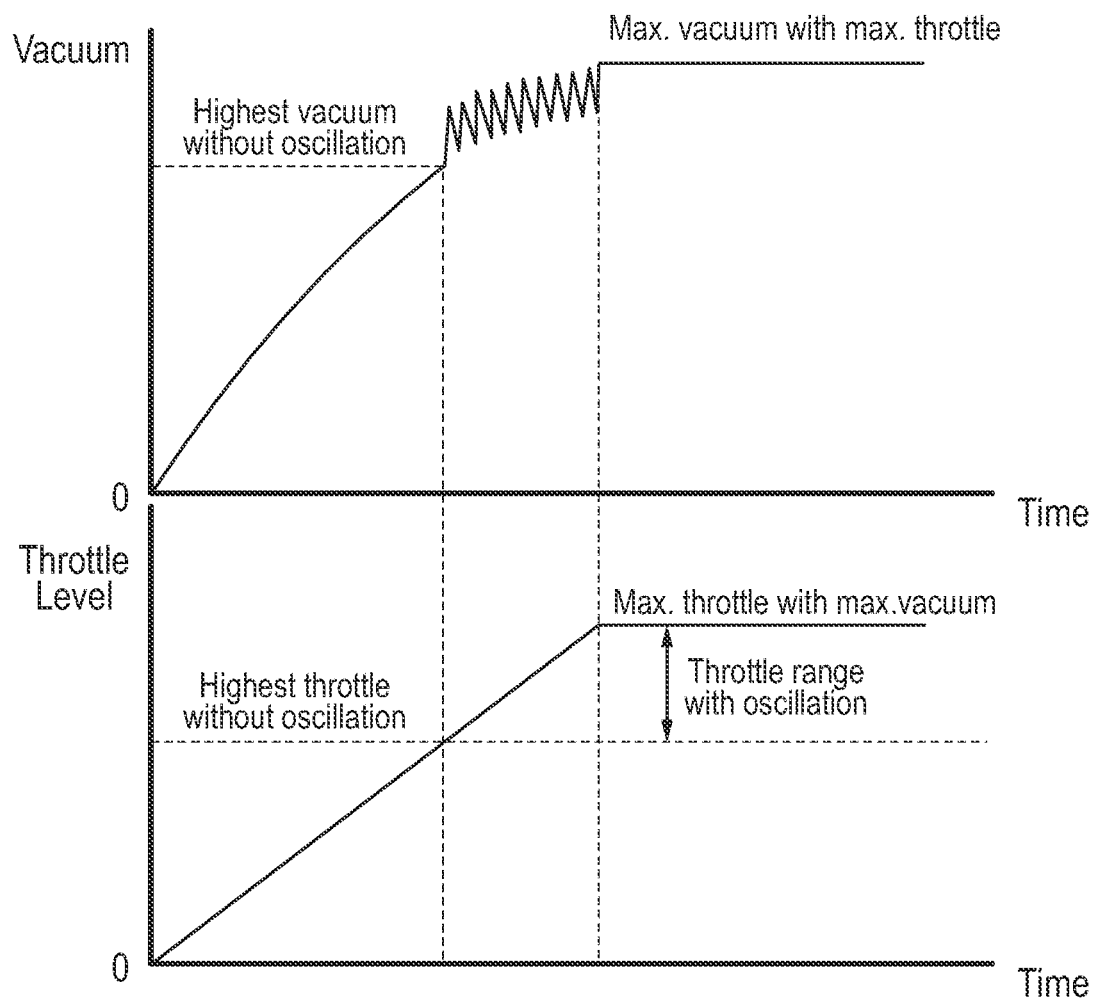
FIG. 1 is an exemplary prior art depiction of vacuum oscillation in a venturi vacuum system in absence of oscillation minimization features.

Referring now to FIG. 1, charts illustrating a conventional venturi vacuum surgical system without oscillation minimization features employed are shown. Specifically, synchronized charts of vacuum pressure changing from 0 to maximum e.g. 670 mmHg as the result of increasing supply pressure or flow in terms of throttle level from 0 to the level corresponding to maximum vacuum are depicted. The throttle level may be the percentage opening of a throttle control proportional valve. Vacuum oscillation occurs in a region just below the maximum vacuum level, e.g. 550—just under 670 mmHg. In such venturi vacuum system, it may be undesirable to operate (or may even be inoperable) in this range because vacuum pressure oscillation resulting in IOP fluctuation can affect the efficiency, efficacy, and safety of the surgical procedures. Once the vacuum reaches maximum e.g. 670 mmHg, however, the oscillation disappears.

Figure 2:
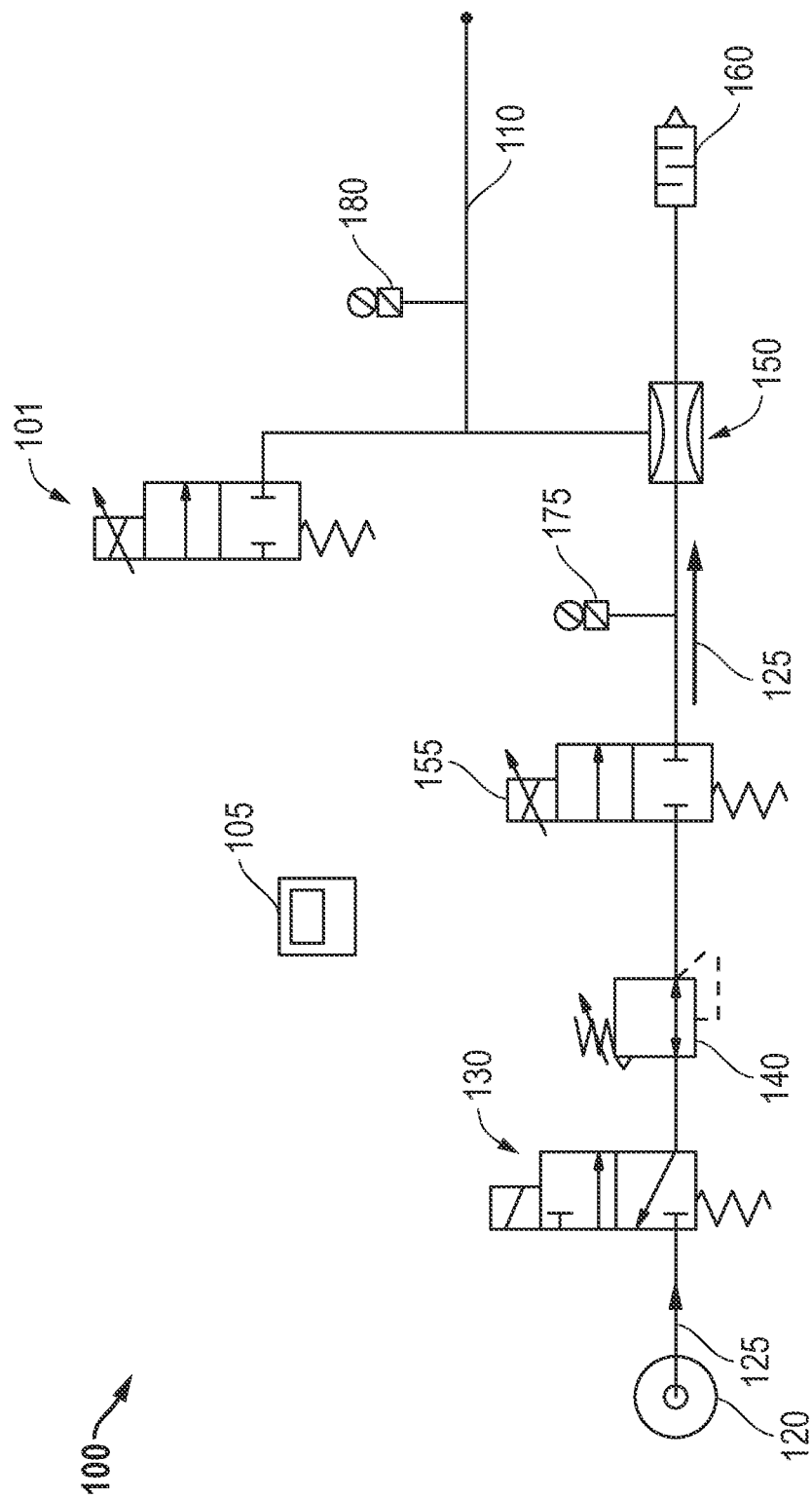
FIG. 2 is a schematic overview of a venturi vacuum surgical system with oscillation minimization features.

Referring now to FIG. 2, a schematic overview of a venturi vacuum surgical system 100 is illustrated that employs features for oscillation minimization. That is, as with other vacuum systems supporting surgical tools in the field, a venturi vacuum generator 150 is employed. The system 100 includes other standard components such as pressure source 120, a pressure regulator 140, shutoff valve 130, throttle device 155, vacuum pressure transducer 180, and muffler 160. However, a conventional system is prone to generate oscillations when such a venturi device is operated at near maximum vacuum. As detailed herein though, the illustrated system 100 employs unique features of venturi inlet pressure transducer 175 and bleed control device 101 to minimize, dampen and/or eliminate such oscillations.

Continuing with reference to FIG. 2, in the system 100 the pressure source 120 generates a fluid flow of air (see 125) toward the noted venturi vacuum generator 150. So, for example, the pressure source 120 may be a pneumatic pressure source that directs 20-40 SLPM (standard litre per minute) of air toward the vacuum generator 150. In terms of a pressure measurement, perhaps about 60 PSI (pounds per square inch) is found at the source 120. Of course, this is only an exemplary circumstance.

In the surgical environment, this source 120 may be drawn from a common line that runs throughout a facility, from a mobile base unit, high pressure cylinder, compressor or other appropriate source. While this degree of pressure to support the airflow 125 is available, a throttle device 155 is provided which is utilized to actually govern the air pressure and flow that reaches the vacuum generator 150. This device 155 may specifically be a throttle control proportional valve as illustrated. So, for example, while 40 SLPM is available, a maximum throttle of about 30 SLPM may be established for the illustrated vacuum generator 150 based on its own design tolerances and maximum efficiency. This, in turn may translate to 60 PSI being available as noted but with the throttle maximum being configured to maximize pressure at about 50 PSI to the venturi vacuum generator 150. Reference to PSI values here are valuable given that real-time pressure readings are available from transducers 175, 180 for the oscillation elimination control methods detailed below.

Continuing with the example of a 50 PSI maximum supplied to vacuum generator 150, it is understood that in the range just below the maximum throttle, (e.g., 45—just under 50 PSI), the generator 150 may be prone to display undesirable oscillations. If not addressed, this could affect performance of a tool at the end of a suction or vacuum line 110 that is facilitated by the system 100. Thus, the vacuum line 110, which is in fluid communication with the venturi generator 150 for sake of generating the noted suction, is also in fluid communication with a bleed control device 101. This device 101 may be a bleed control proportional valve, which, when operated in concert with other features of the system 100 as described below, may be utilized to dampen or substantially eliminate the noted oscillations.

The system 100 of FIG. 2 further includes a venturi inlet pressure transducer 175 that is located in the fluid path between the throttle device 155 and the venturi vacuum generator 150. Thus, real-time monitoring of the actual throttle level via detected pressure at the transducer 175 may be kept track of. Specifically, detected pressure may be monitored by a system controller 105 with suitable computing capability. Thus, the controller 105 may further adjust the throttle level at the device 155 based on the actual detected pressure from the transducer 175 in a standard feedback manner. For example, where a throttle seen at 40 PSI to the venturi vacuum generator 150 is desired but a pressure detection more indicative of 45 PSI has been made at the transducer 175, the controller 105 may make the appropriate adjustment to the throttle device 155.

In the embodiment shown, the controller 105 sits apart from the throttle device 155 and venturi inlet pressure transducer 175 but may communicate as noted via wireless means. Alternatively, system components including these features and others for which controller communications are desirable may be wired together as part of a single mobile or stationary unit.

Continuing with reference to FIG. 2, the flow 125 through the venturi generator 150 exits toward a muffler device 160. Of course, as with other venturi generator devices, the illustrated generator 150 also includes a flowline for vacuum communication away from the generator and ultimately toward the vacuum line 110 as noted above. That is, the flow 125 through the generator 150 ultimately facilitates a vacuum at the vacuum line 110, for example, to support a surgical procedure as illustrated in FIG. 3.

Perhaps more notably, however, the system embodiment depicted in FIG. 2 also includes vacuum communication toward a bleed control device 101 as noted above. As detailed below, this device 101 may be actuated to divert vacuum pressure away from the vacuum line 110 when pressures are in a region that is prone to support oscillation. So, for example, where the venturi generator 150 is rated to support an efficient maximum vacuum of about 670 mmHg, it may also tend to display vacuum oscillations when suction is in the 550-670 mmHg range if measures to avoid the oscillations are not taken. Of course, this is only by way of example. A variety of other maximums and potential oscillation ranges may be considered. Regardless, in sticking with the given example, a vacuum pressure transducer 180 may be placed in fluid communication with the venturi generator 150. So, for example, as the throttle is increased at the throttle device 155, tracking the approaching predetermined oscillation region of 550-670 mmHg of concern may occur on the vacuum side of the venturi generator 150.

Continuing with the 670 mmHg maximum venturi generator 150 example, recall that a more than sufficient pressure supply 120 is available which facilitates an airflow 125 that is modified by the throttle device 155 as it passes to and through the venturi generator 150. So, for example, at the outset of operations, the throttle device 155, may be directed by the controller 105 to steadily increase pressure reaching the generator 150 beginning with 0 PSI and reaching about 45 PSI. This can be confirmed by the inlet pressure transducer 175 throughout this initial ramping up of the pressure. Once more, the true effect of this ramping up on the suction side may also be monitored directly by the vacuum pressure transducer 180. For example, these detections may confirm whether the ramping up resulted in an expected corresponding ramping up of vacuum from 0 to 550 mmHg. Further, to the extent that the ramping up was more (or less) than expected on the vacuum side, the throttle level may be correspondingly lowered (or raised) as directed by the controller 105.

Figure 3:
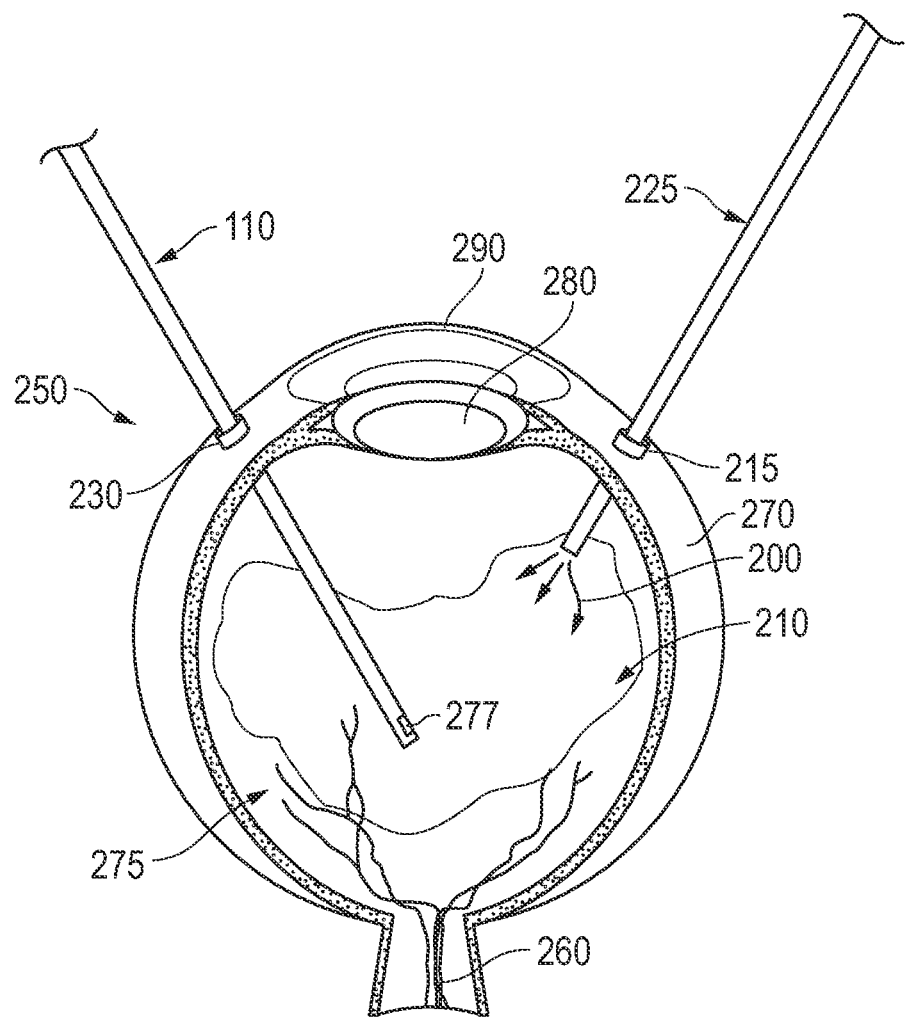
FIG. 3 is an overview of a vitrectomy procedure performed on a patient's eye with the support of the venturi vacuum system of FIG. 2.

Continuing further with the example above, suction through the vacuum line 110 may be applied across the entire range of 0-550 mmHg in support of a procedure as illustrated in FIG. 3. However, where the oscillation region comes into play, at 550-670 mmHg in this example, alternative measures may be taken to allow the vacuum line 110 to effectively avoid any notable oscillation to the procedure. Specifically, as alluded to above, once the detected vacuum reaches the oscillation region at 550 mmHg, the bleed device 101 may be employed to begin bleeding vacuum pressure from the venturi generator 150. At the same time, the throttle is increased at the throttle device 155 so that the venturi vacuum generator 150 produces higher vacuum to cover the vacuum bleeding. The net effect is that vacuum level at the vacuum line 110 is maintained at 550 mmHg but without oscillation. As detailed below, the oscillation region may be predetermined or the controller 105 may be configured for responsiveness to actually detected oscillation from the vacuum pressure transducer 180.

Recall that the oscillations are a natural effect of pressure directed at the generator 150 (e.g. 45-50 PSI in the present example). In the present example, this is translated on the vacuum side to oscillations at 550-670 mmHg. Thus, the bleed device 101, a proportional valve, may be opened during exposure to these pressure ranges while the throttle is increased to a higher level. In this manner, a vacuum of 550-670 mmHg in the vacuum line 110 can be achieved and corresponding oscillations in this operating region would not present. This is detailed further below.

Referring specifically now to FIG. 3, a side cross-sectional overview of a patient's eye 250 is illustrated during a vitrectomy procedure. Specifically, the procedure is supported by the vacuum line 110 of the system 100 of FIG. 2. As illustrated, this line 110 is part of a vitrectomy probe needle which terminates at a port 277 for the uptake of vitreous humor 210 from the eye 250. At the same time, an infusion tool 225 is used to deliver an inert biocompatible fluid 200 into the eye 250, replacing the removed vitreous humor and helping to maintain a pressure balance therein. Thus, stability of the vacuum through the line 110 assists in maintaining the pressure inside the eye (Intraocular Pressure (IOP)).

Continuing with reference to FIG. 3, the probe needle 110 and the infusion tool 225 are supported by pre-placed cannulas 230, 215. This provides guided support to the devices for the procedure. The cannulas 215, 230 are small in diameter and relatively short in length. This helps avoid risk of damage to the optic nerve 260, retina 275 and other more delicate features at the back of the eye 250. Notice that the cannulas 215, 230 are positioned in an offset manner at the sclera 270. In this way, damage to the more delicate cornea 290 and lens 280 may be avoided. Thus, a variety of measures are taken to help ensure that unintentional injury is avoided during the procedure. It is along similar lines that embodiments of the present application are directed at avoiding unintended movement of optic nerve 260, retina 275, cornea 290 and lens 280 caused by unstable IOP as a result of vacuum pressure oscillation in vacuum line 110 during the procedure. Specifically, employing the system 100 of FIG. 2 to supply the vacuum to the line/needle 110 of FIG. 3, means that any sudden or unexpected change of IOP may be largely, if not completely, eliminated to avoid unintentional injury during the procedure.

Figure 4:
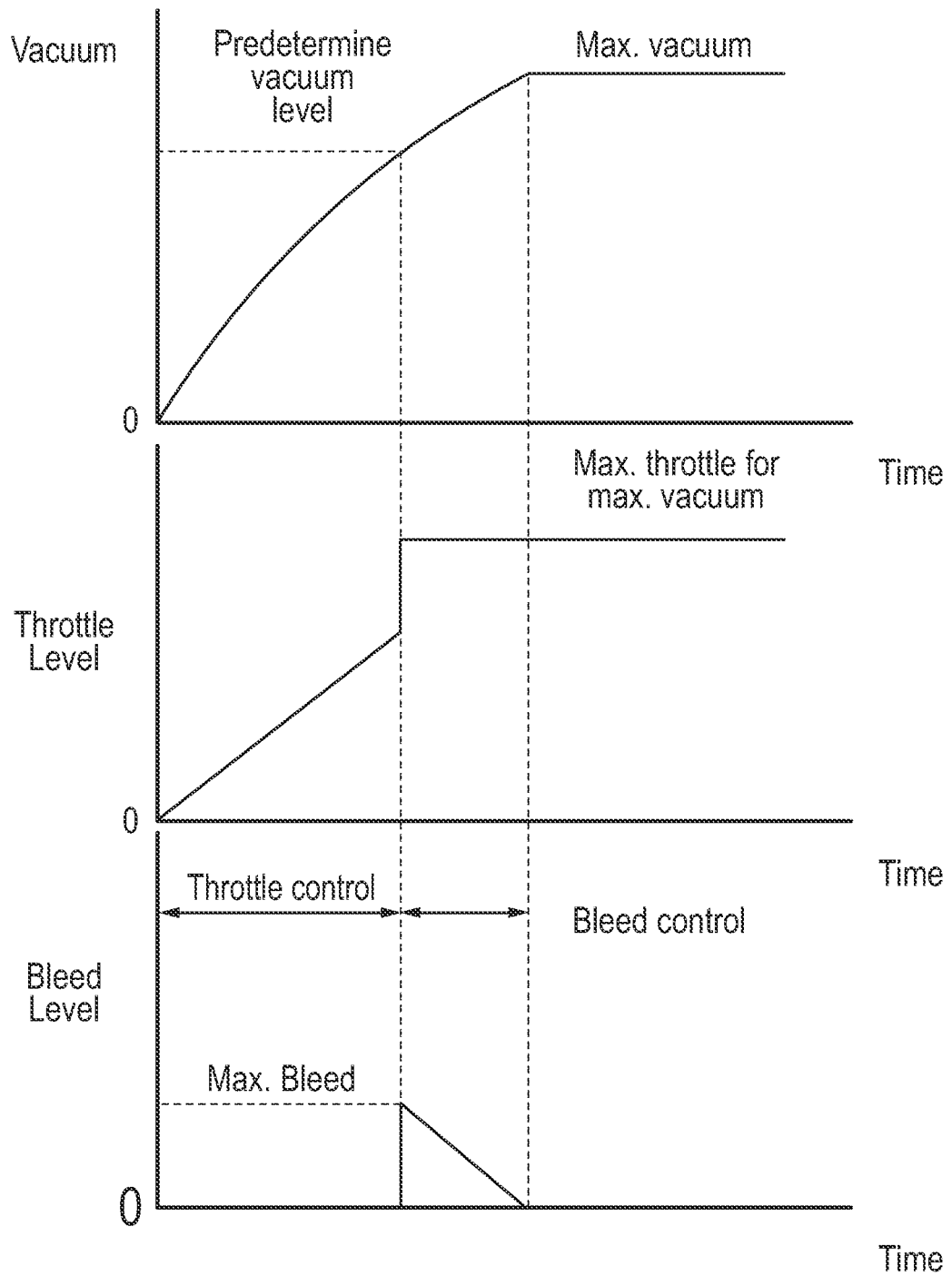
FIG. 4 is a chart depicting a control method applied in the venturi vacuum system of FIG. 2 to minimize or eliminate oscillation during the procedure of FIG. 3.

Referring now to FIG. 4, a chart depicting a venturi vacuum surgical system 100 with oscillation minimization features employed is illustrated. Specifically, synchronized charts of vacuum pressure changing from 0 to maximum (e.g. 670 mmHg) as the result of controlling supply pressure or flow throttle level and vacuum bleed level to eliminate oscillation is shown. The throttle level may be the percentage opening of a throttle control proportional valve 155. The vacuum bleed level may be the percentage opening of a vacuum bleed control proportional valve 101.

In FIG. 4, the top chart's vertical axis indicates the degree of vacuum beginning with no vacuum at the bottom. With reference to the discussion above, recall that the throttle device 155 of FIG. 2 may be used to dictate an increasing airflow 125 to the venturi vacuum generator 150, ultimately increasing this vacuum over time. The middle chart's vertical axis indicates the level of throttle, which may be a percentage opening of a throttle control proportional valve 155. As discussed above, the venturi vacuum surgical system 100 may employ a bleed device 101 for bleeding vacuum pressure from the venturi generator 150 when needed. The bottom chart's vertical axis indicates the level of bleed, which may be a percentage opening of a bleed control proportional valve 101. In the charts of FIG. 4, the horizontal axes are synchronized to represent the passage of time as the vacuum changes as the result of throttle level and bleed level change indicated at the vertical axes.

Referring again to FIG. 1, recall that a conventional venturi vacuum surgical system without oscillation minimization features employed may display a fair amount of vacuum oscillation in a region just below the maximum vacuum level, e.g. 550-670 mmHg in the present example. However, once the vacuum reaches a maximum e.g. 670 mmHg, the oscillation may disappear. Continuing here with reference to FIG. 4, rather than allow this oscillating range of vacuum to present through the vacuum line 110 of FIG.

2 (continuing to the probe needle 110 of FIG. 3), the system 100 employs an oscillation elimination control method as illustrated at FIG. 4.

At a predetermined vacuum level (e.g. at 540 mmHg) below the region of oscillation (e.g. 550-670 mmHg) the throttle may be immediately taken to its maximum as illustrated in FIG. 4 where it is maintained. At this same point in time, a bleed level (e.g., a maximum bleed level) may be applied through the bleed device 101 of FIG. 2. As shown in FIG. 4, this bleed may dropped over time as needed so that vacuum level from 540 mmHg to 670 mmHg is obtained, and at a low bleed level (e.g. 0 bleed), a maximum vacuum 670 mmHg may be maintained. The effect of FIG. 4 control method employed in venturi vacuum surgical system 100 is that full range of vacuum level e.g. 0-670 mmHg may be achieved without oscillation.

With added reference to FIG. 2, the above described control method may be managed by the controller 105 of FIG. 2. For example, the vacuum level may be monitored at the vacuum transducer 180. When a predetermined vacuum level is reached, say 540 mmHg or just below 550 mmHg, the throttle device 155 is taken to its maximum as noted to correspond with the maximum vacuum (e.g. 670 mmHg). By the same token, a confirming pressure read of 50 PSI may be noted at the inlet transducer 175. Maximum bleed may be simultaneously applied as noted at this time. The processor of the controller 105 may specifically employ a PID (proportional-integral-derivative) algorithm based on real-time venturi vacuum pressure and inlet pressure detections to adjust the throttle and bleed levels thereafter to obtain vacuum levels from 540 to 670 mmHg and to maintain maximum vacuum (e.g., at 670 mmHg).

Figure 5:
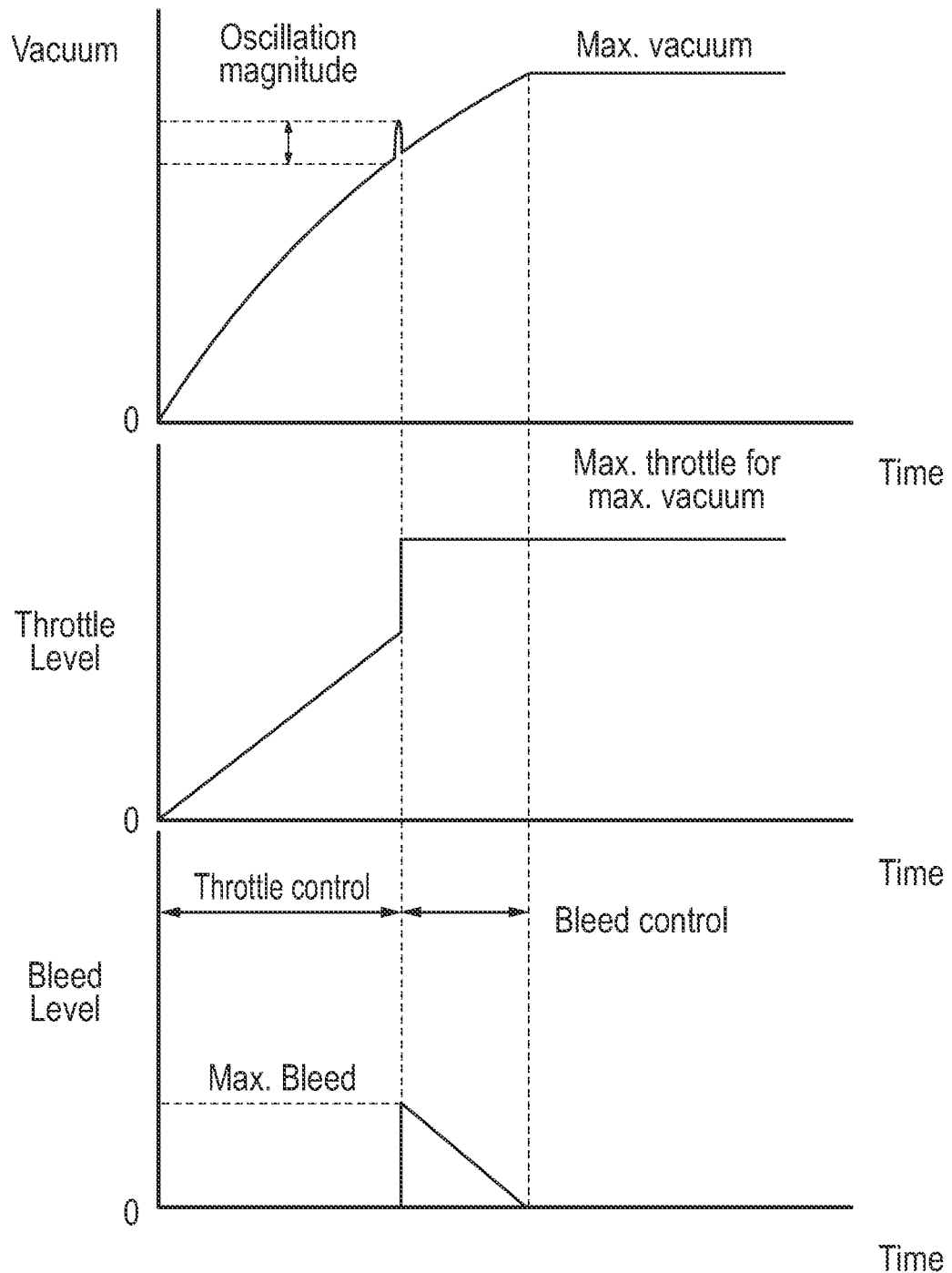
FIG. 5 is another chart depicting another control method applied in the venturi vacuum system of FIG. 2 to minimize or eliminate oscillation during the procedure of FIG. 3.

Referring specifically to FIG. 5, predetermined vacuum levels are not utilized as the control method illustrated in FIG. 4. Instead, the controller 105 of FIG. 2 may initiate such PID control over the throttle and bleed upon initial detection of oscillation. The determination of oscillation can be based on sudden change of vacuum level without being commanded for and the magnitude of change is bigger than a predetermined threshold so that noise signal will not cause a false determination. For example, if the predetermined threshold is set to 20 mmHg, an initial oscillation greater than 20 mmHg may trigger the oscillation control method. As seen in FIG. 5, an initial oscillation is shown, which may be vacuum jumping (at 550 mmHg) in magnitude over the 20 mmHg threshold. Once controller 105 detects that, the same PID algorithm may be applied as what is in FIG. 4 thereafter (i.e., the throttle may be immediately taken to its maximum and a bleed level may be applied through the bleed device 101 to obtain the desired vacuum).

Given the millisecond response time capabilities of such a system 100 in its PID control algorithm to obtain the desired vacuum level in vacuum line 110, it is unlikely that this manner of detecting initial oscillation and or sudden jumps of throttle level and bleed level would result in any measurable oscillation as felt by the surgeon during a procedure as illustrated in FIG. 3.

Of course, it may also be advantageous to avoid sudden jumps in throttle level and bleed level. Thus, in one embodiment, a more transitional approach to increasing the throttle and introducing the bleed may occur. In this embodiment, the throttle increase is more steady with the bleed introduced well before reaching the lower end of the oscillation region. It may be advantageous to begin the bleed and throttle coordination efforts much earlier than just below the oscillation region. Specifically, with reference to FIG. 6, a chart illustrating such a transitional approach is shown. Within the transition control vacuum range, both throttle level and bleed level are under PID control for achieving the commanded vacuum level. Outside the transition control vacuum range, all controls are the same as the control methods in FIG. 4.

Figure 6:
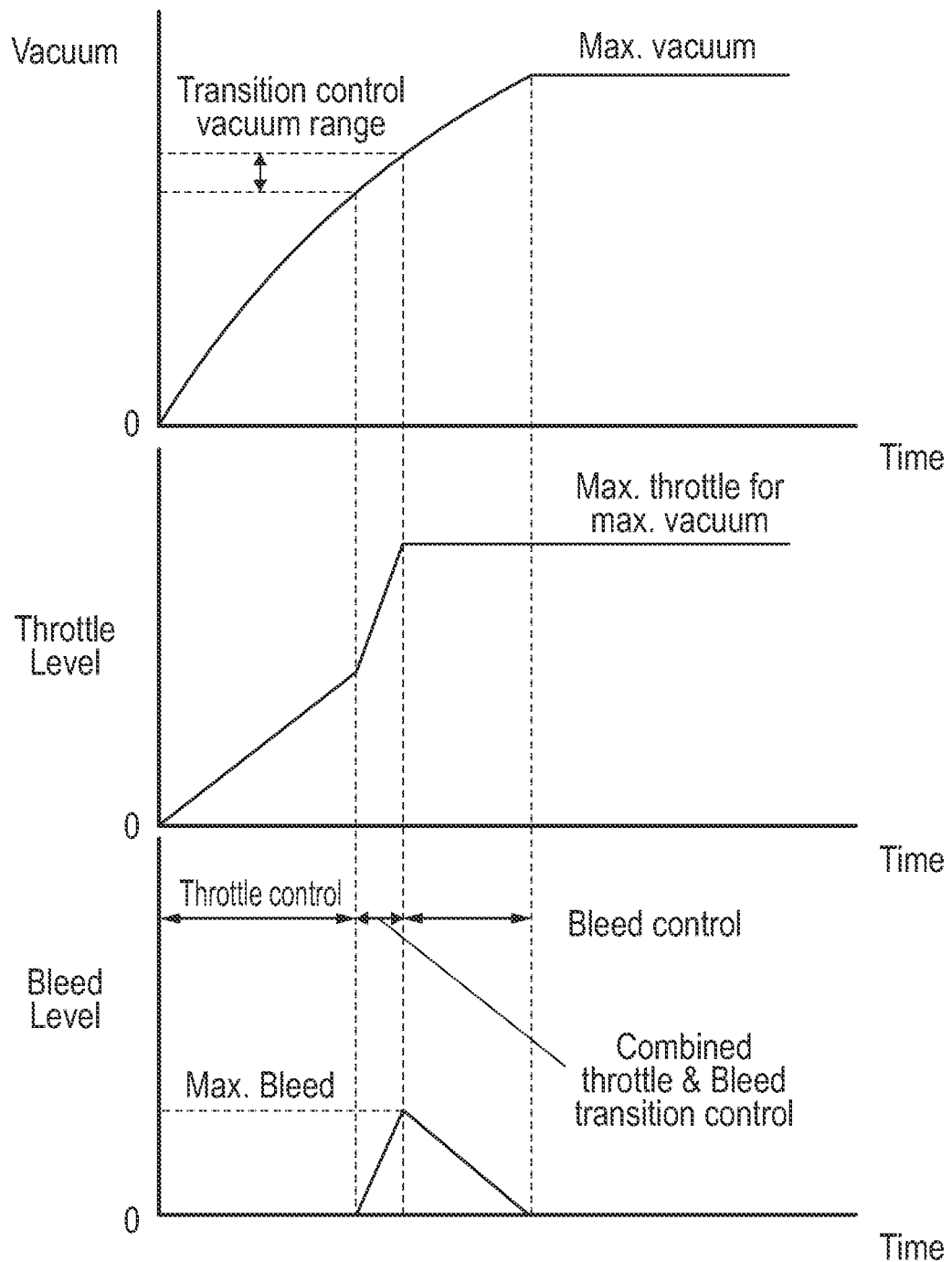
FIG. 6 is yet another chart depicting another control method applied in the venturi vacuum system of FIG. 2 to minimize or eliminate oscillation during the procedure of FIG. 3.

Although not clearly shown, it is apparent that the vacuum level increases more steadily in FIG. 6. Note that the time reflected at the horizontal axes accounts for a brief period where the throttle is more steadily increased to its maximum, perhaps over about 5-20 milliseconds (see the middle chart). With reference to the lower chart, the same steady increase to the bleed is also reflected over this same period of time.

Notice that after the transitional period, the maintenance of the throttle at maximum and the draw down of the bleed proceeds as before. However, as a practical matter, the vacuum range is more steady. For example, note the absence of the initial vacuum jump for the top chart of FIG. 5. Furthermore, both throttle level and bleed level are changing gradually which avoids momentary vacuum level fluctuation and long settling time associated with sudden jumps of throttle level and bleed level. Ultimately, an enhanced control method is hereby provided.

Figure 7:
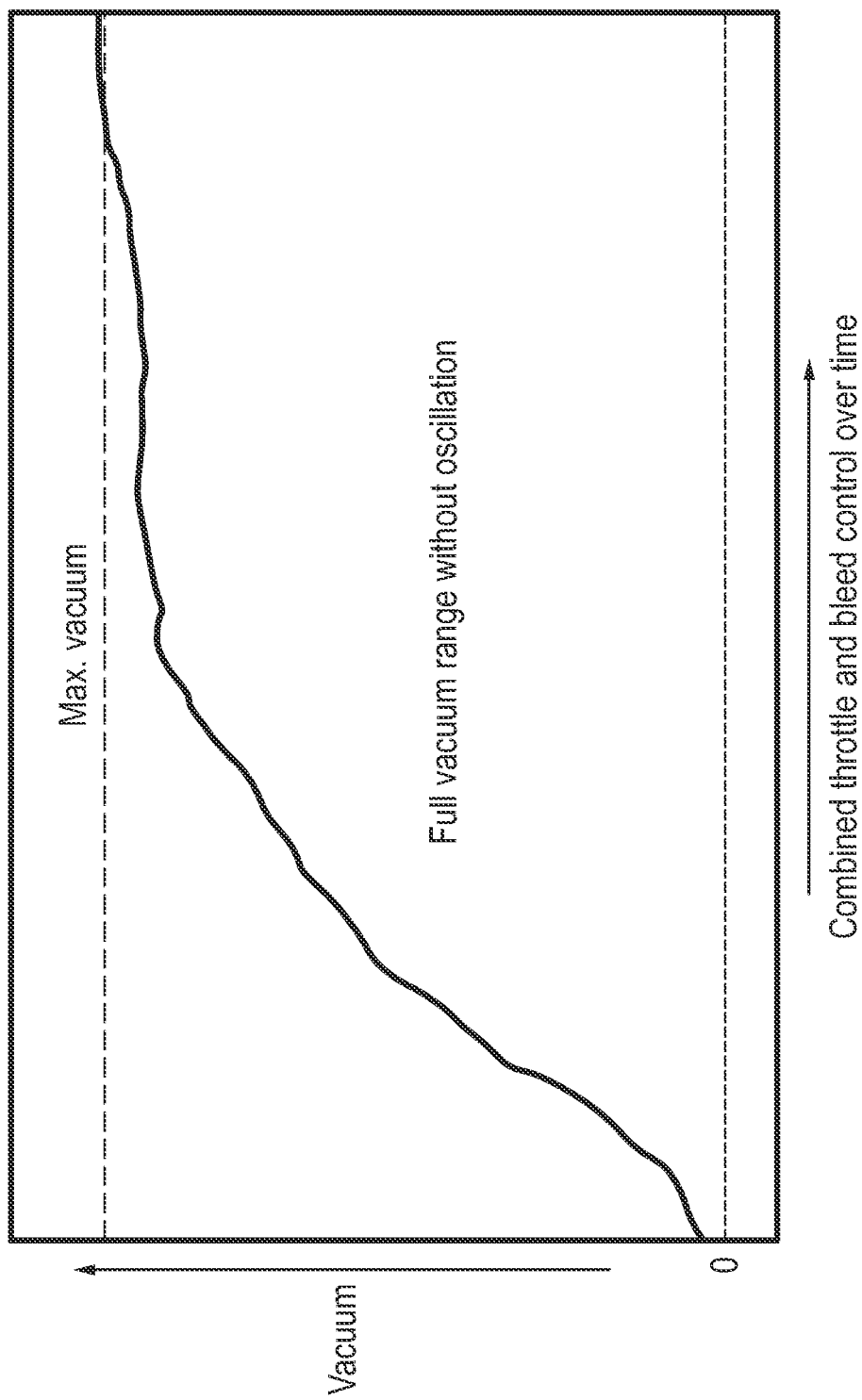
FIG. 7 is a chart depicting an oscillation-free vacuum attained from application of any of the control methods of FIGS. 4, 5, and 6.

Indeed, referring specifically now to FIG. 7, a chart depicting the oscillation-free vacuum attained from application of control method of FIG. 6. is illustrated. Notice that a full vacuum range is made available without oscillations or sudden vacuum jumps.

Figure 8:
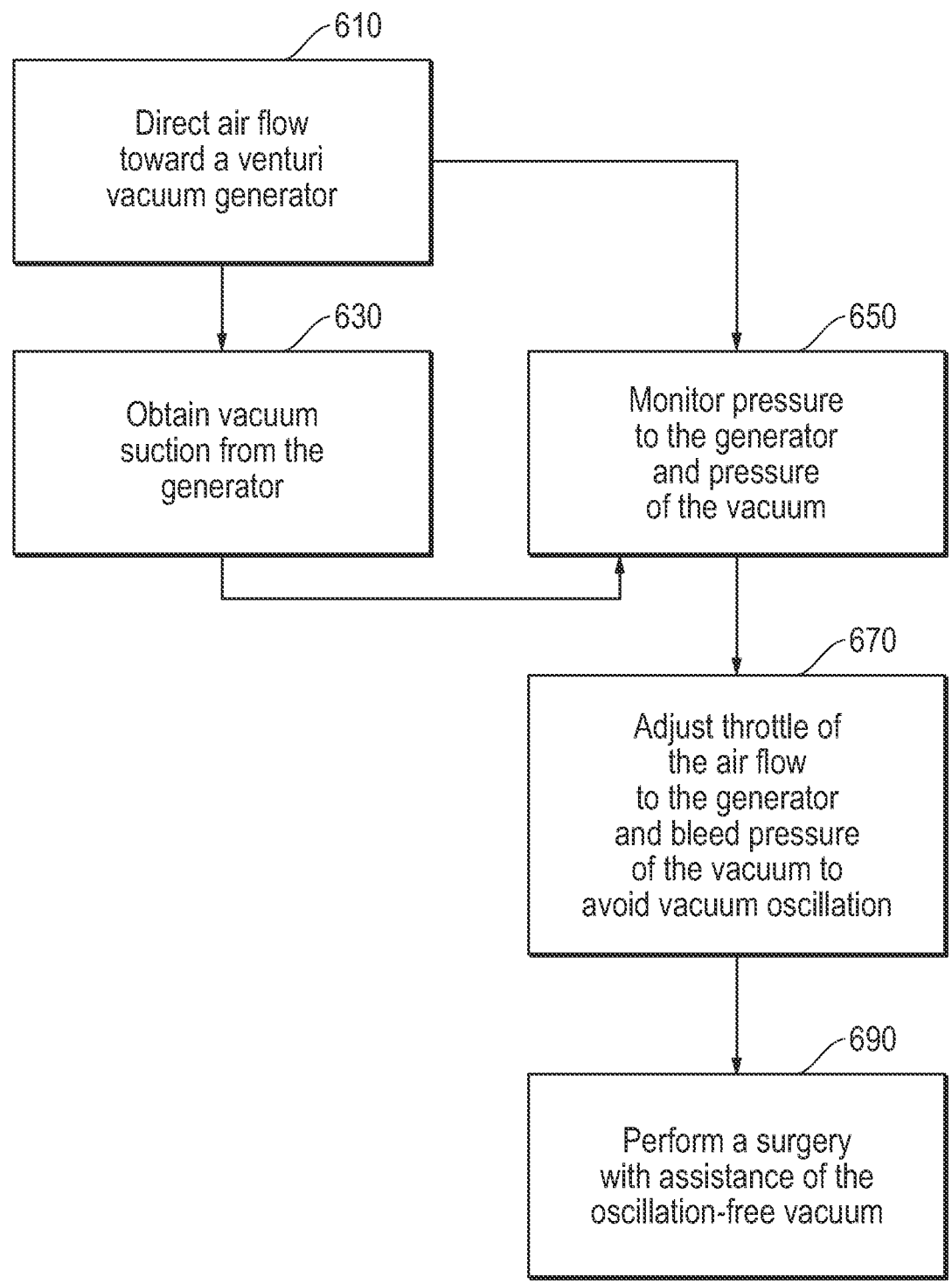
FIG. 8 is a flow-chart summarizing an embodiment of employing a venturi vacuum system and control methods for minimizing or eliminating oscillation during a surgical procedure.

Referring now to FIG. 8, a flow-chart summarizing an embodiment of employing a venturi vacuum system is illustrated. Namely, as indicated at 610 and 630 an airflow is directed at a venturi vacuum generator for obtaining a vacuum suction therefrom. Pressure may be monitored in terms of both the airflow to the vacuum generator and the generated vacuum as noted at 650. Thus, a processor may adjust a throttle of airflow to the vacuum generator and cooperatively bleed pressure of the vacuum to avoid vacuum oscillation (see 670). Ultimately, as indicated at 690, an oscillation free vacuum is provided for use in supporting a surgical procedure.

Embodiments described hereinabove include a venturi facilitated vacuum system with the unique ability to substantially prevent oscillations from reaching a surgical suction tool supported by the system. Avoiding the effect of oscillations on a surgical tool as detailed herein not only provides the surgeon with a more stable manner of performing surgery but also affords continuous vacuum assistance without the need to halt a procedure. That is, the need to pause a procedure or operate only outside of certain regions of vacuum assistance may be avoided. Rather, the surgeon is now afforded continuously usable suction power throughout the procedure in the full vacuum range of 0 to maximum.

The preceding description has been presented with reference to presently preferred embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A method of generating a venturi vacuum, the method comprising:
   directing a regulated pressure supply from a pneumatic pressure source to a venturi vacuum generator to provide a vacuum to a vacuum line;
   monitoring inlet pressure to the venturi vacuum generator with a venturi inlet pressure transducer;
   monitoring vacuum pressure of the vacuum line connected to the venturi vacuum generator with a vacuum pressure transducer;
   obtaining monitored inlet and vacuum pressure values at a system controller; and
   adjusting at least one of a throttle level of the regulated pressure supply to the venturi vacuum generator and a vacuum pressure bleed level from the vacuum line with the system controller based on the monitored values to substantially prevent vacuum oscillation in the vacuum line.

2. The method of claim 1 wherein the adjusting further comprises:
   employing a throttle control proportional valve to maintain the throttle level at a maximum throttle to prevent vacuum oscillation; and
   employing a bleed control proportional valve to control the vacuum pressure bleed level to achieve an operator determined vacuum level.

3. The method of claim 1 wherein the adjusting further comprises:
   maintaining a set vacuum bleed level for the preventing of the vacuum oscillation; and
   employing a throttle control proportional valve to achieve an operator determined vacuum level.

4. The method of claim 1 wherein the adjusting further comprises:
   detecting a predetermined vacuum level below a vacuum level oscillation region;
   moving a throttle control proportional valve to a maximum corresponding to a maximum vacuum for the venturi vacuum generator;
   opening a bleed control proportional valve to a predetermined maximum level based on the detecting;
   employing a PID (proportional-integral-derivative) control algorithm at the system controller in coordination with the monitored values to adjust a throttle control proportional valve to maintain a maximum venturi inlet pressure; and
   adjusting a bleed control proportional valve to achieve an operator determined vacuum pressure level.

5. The method of claim 1 wherein the adjusting further comprises:
   detecting a predetermined vacuum level below a vacuum level oscillation region;
   employing a PID control algorithm at the system controller and accounting for the monitored values in real-time to adjust a throttle control proportional valve and a bleed control proportional valve to attain an operator determined vacuum level within a predetermined transitional vacuum range upon the detecting of the predetermined vacuum level;
   detecting a vacuum level exceeding a predetermined transitional vacuum range but below the vacuum level oscillation region;
   employing the PID control algorithm to adjust the throttle control proportional valve to a maximum corresponding to a maximum vacuum for the venturi vacuum generator; and adjusting a bleed control proportional valve to achieve an operator determined vacuum pressure level.

6. The method of claim 1 wherein the adjusting further comprises:
   detecting vacuum level oscillation from the vacuum pressure transducer;
   opening a throttle control proportional valve to a maximum corresponding to a maximum vacuum for the venturi vacuum generator;
   opening a bleed control proportional valve to a predetermined maximum level; and
   employing a PID control algorithm at the system controller and accounting for the monitored values in real-time to ensure maintenance of the throttle control proportional valve at the maximum and to adjust the bleed control proportional valve to provide an operator determined vacuum level.

* * * * *